United States Patent [19]
Howlett

[11] Patent Number: 6,082,355
[45] Date of Patent: Jul. 4, 2000

[54] INHALATION APPARATUS

[75] Inventor: David John Howlett, King's Lynn, United Kingdom

[73] Assignee: Bespak plc, United Kingdom

[21] Appl. No.: 09/031,668

[22] Filed: Feb. 27, 1998

[30] Foreign Application Priority Data

Mar. 3, 1997 [GB] United Kingdom .................... 9704363

[51] Int. Cl.[7] .................................................. A61M 11/00
[52] U.S. Cl. ................................ 128/200.23; 128/200.14; 128/200.22; 128/203.12
[58] Field of Search ..................... 128/200.23, 200.14, 128/200.21, 200.22, 203.12, 203.24, 203.13, 203.14

[56] References Cited

U.S. PATENT DOCUMENTS

| | | | |
|---|---|---|---|
| 3,789,843 | 2/1974 | Armstrong et al. | 128/200.23 |
| 4,414,972 | 11/1983 | Young et al. | 128/200.23 |
| 5,184,761 | 2/1993 | Lee | 128/200.23 |
| 5,217,004 | 6/1993 | Blasnik et al. | 128/200.23 |
| 5,224,472 | 7/1993 | Pesenti et al. | 128/200.23 |
| 5,447,150 | 9/1995 | Bacon | 128/200.23 |

FOREIGN PATENT DOCUMENTS

0147028 A1   7/1985   European Pat. Off. .

*Primary Examiner*—John G. Weiss
*Assistant Examiner*—V. Srivastava
*Attorney, Agent, or Firm*—Smith, Gambrell & Russell, LLP

[57] ABSTRACT

Inhalation apparatus for dispensing a product comprises a housing (2) having a cylindrical portion (6) adapted to receive a pressurized dispensing container (3) and a mouthpiece (7). The apparatus includes a duct (18) communicating with the container receiving portion for conveyance of product towards the mouthpiece. An air inlet valve provided by a vent hole (14) and an actuator (19) is provided and is biased with a first position sealing the air inlet. The actuator is manually movable to a second position in which the air inlet is unsealed and allows air to flow into the housing and through the mouthpiece for any user applied suction to the mouthpiece and to a third position for the dispensing of a product into the resulting air flow. The movement between the second and third positions delays the discharge of the product until air flow through the device has been established.

14 Claims, 1 Drawing Sheet

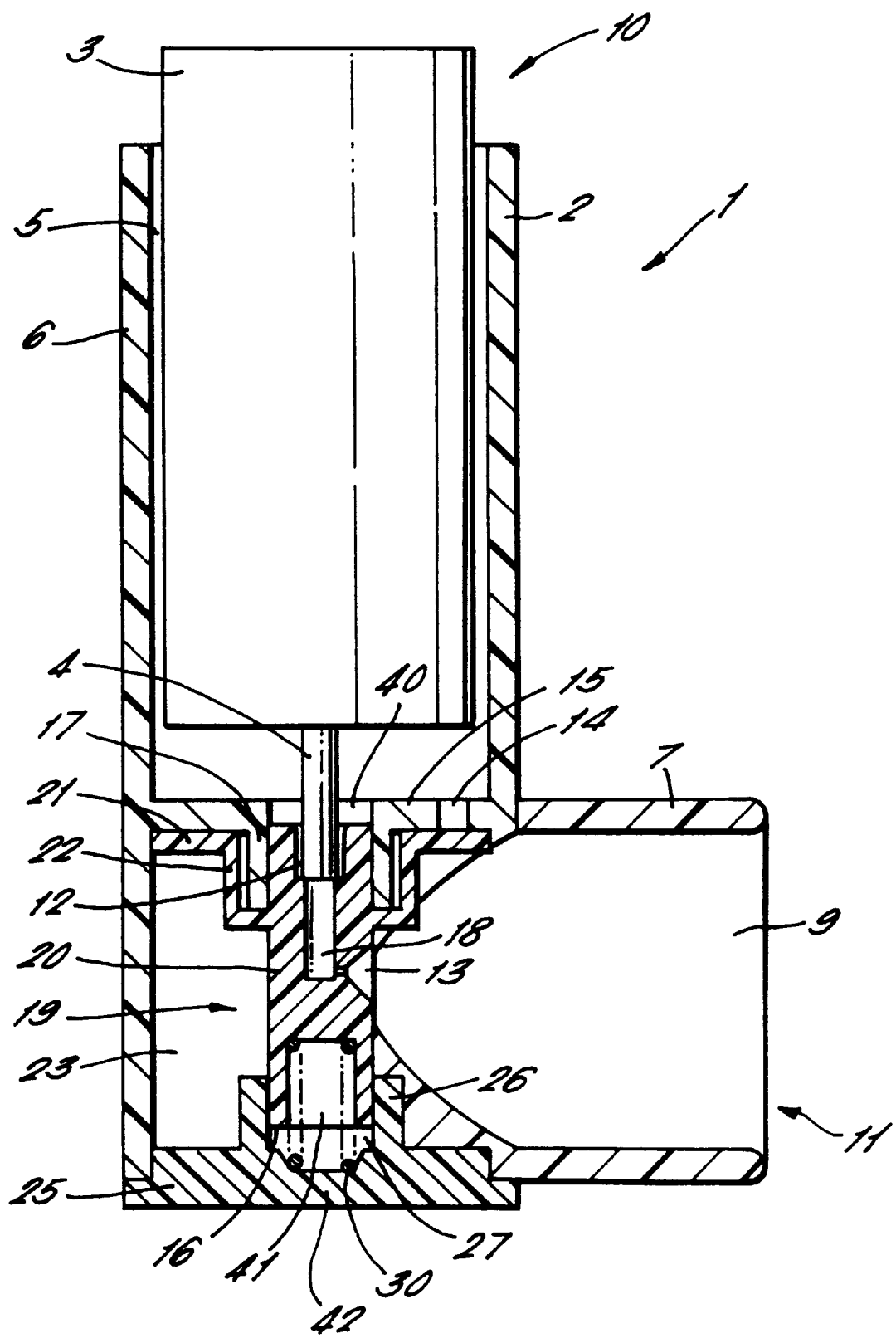

INHALATION APPARATUS

BACKGROUND

This invention relates to an inhalation apparatus for dispensing substances for inhalation and, in particular, but not exclusively, for dispensing medicinal products in aerosol form from a pressurised dispensing container.

It is known to provide a sensor in an inhalation apparatus to detect inhalation by the user in order to synchronise with inhalation the release into the inhaled airflow the substance to be inhaled. It is, for example, important in the administration of aerosol products for the relief of asthma that the timing of the dispensing operation should be carefully controlled to ensure maximum deposition of substance in the user's lungs.

It is known from GB 2266466 to provide an electrically operated dispensing means responsive to a signal generated by a sensor which is responsive to a flow of air through a passageway. The disadvantage of this solution is that the apparatus is expensive.

An object of the present invention is to provide dispensing means in which mechanical means are used to co-ordinate the release of the substance with the inhalation.

SUMMARY OF THE INVENTION

The present invention therefore provides an inhalation apparatus for dispensing a product comprising a housing having a portion adapted to receive a pressurised dispensing container and a mouthpiece, said apparatus further comprising duct means communicating with the container receiving portion for conveyance of product towards the mouthpiece, air inlet valve means comprising at least one air inlet for allowing air into the housing and an airflow controller biased to a first position sealing said air inlet and being manually movable to a second position in which the air inlet is unsealed and allows the air to flow into the housing and through the mouthpiece when a user applies suction to the mouthpiece and to a third position for the dispensing of a product into the resulting air flow, the movement between the second and third positions providing means for delaying the discharge of the product until the air flow has been established.

An advantage of the present invention is that the dispensation of the medicament is synchronised with inhalation of the user using an inexpensive inhalation apparatus.

Preferably, the airflow controller provides a bore for receiving a valve stem of a dispensing container and duct means connecting the valve stem with the mouthpiece.

Preferably, the housing comprises a partition separating the housing into an upper cylindrical portion for receiving a dispensing container and a lower portion housing the airflow controller, wherein the air inlet is located in the partition and the airflow controller has a sealing disc engagable with said partition to cover the air inlet.

Preferably the airflow controller is axially slidable within a socket provided on the partition and is spring biased so that the sealing disc is in sealing contact with the partition.

Preferably movement of the air flow controller between the first and third positions comprises lost motion.

The "lost motion" ensures that the user inhales for a finite period before the dispensation of the medicament, increasing the amount of medicament deposited in the user's lungs.

Preferably, stop means are provided by an end cap of the housing to prevent movement of the air flow controller beyond the third position.

Preferably the spring constant of the spring is such that a greater force is required to depress, in use, a valve stem of a dispensing container inserted into the apparatus, than that required to compress the spring.

Advantageously, the actuator and sealing disc form a single moulded component for reducing manufacturing and assembling costs. The low load-high deflection response spring ensures that the dispensing container is not prematurely actuated at the same time as ensuring that the sealing disc is in sealing engagement with the vent hole before depression of the dispensing container.

A preferred embodiment of the present invention will now be described, by way of example only, with reference to the accompanying drawing of which:

BRIEF DESCRIPTION OF THE DRAWINGS

FIG. 1 is a sectional view of the inhalation apparatus.

DETAILED DESCRIPTION

The apparatus 1 of FIG. 1 comprises a housing 2 consisting of a cylindrical portion 6, open at its upper end to allow air into the apparatus 1 and to receive a cylindrical pressurised dispensing container 3, and a mouthpiece 7 projecting laterally from the lower end of the cylindrical portion 6. With the container 3 inserted in the cylindrical portion 6 there exists a space 5 between the container 3 and the inside surface of the cylindrical portion 6 adequate to allow airflow therethrough. The cylindrical portion 6 is divided into an upper and a lower section by an annular partition 15. Projecting from a lower side of the partition 15 is an annular socket 17 defining a central axial bore 40. Air inlet valve means are provided by a vent hole 14 located in the annular wall of the partition 15, and an actuator 19.

The actuator 19 has a cylindrical body 20, in an upper end of which is a bore 12 for receiving a valve stem 4 of the dispensing container 3. The valve stem receiving bore 12 communicates via a duct 18 with an opening 13 in the side wall of the actuator body 20 which is arranged to direct an aerosol spray through 90° on discharge through the valve stem receiving bore 12 in a direction towards an outlet 11 of the mouthpiece 7. A recessed blind bore 41 is provided in a lower end of the actuator body 20.

An upper end of the actuator body 20 is located within socket 17. The actuator 19 also has, surrounding an upper end of the body 20, a tubular extension 22 supporting an annular actuator sealing disc 21. The sealing disc 21 engages and seals the lower surface of the partition 15, covering the vent hole 14, thus providing an airflow controller.

The lower section of the cylindrical portion 6 of the housing 2 defines a chamber 23, which communicates with the mouthpiece 7, and in which is located the actuator 19. The chamber 23 is closed by an end cap 25. The end cap 25 is push-fitted onto the end of the housing 2. Projecting inwardly from the end cap 25 is an annular socket 26 for receiving a lower end of the actuator body 20 which is free to slide axially therein. A spring 30 has one end positioned in a shallow recess 42 inside the socket 26 on the end cap 25 and its other end in the recessed bore 41 in the lower end 16 of the actuator body 20.

The parameters of the spring 30 are such that the force required to compress the spring 30 is less than that required to depress the valve stem 4. The spring 30 biases the actuator 19 so that the sealing disc 21 is in sealing contact with the partition 15 closing the vent hole 14. In this position, a gap 27 is defined between the lower end 16 of the actuator body 19 and the end cap 25. The gap 27 provides "lost motion" for the actuator 19 during operation of the apparatus 41, as will be described below.

In operation, the user inserts the mouthpiece 7 into his mouth and inhales. Initially, as the vent hole 14 is sealed by the actuator sealing disc 21, there is no airflow into the air passageway 9. Whilst continuing to inhale, the user manually depresses the dispensing container 3 causing the valve stem 4 to move downwardly. In turn, this causes the actuator 19 to slide axially downwards and compress spring 30. The actuator sealing disc 21 is thus moved out of contact with the vent hole 14 allowing the passage of air along the space 5 in the tubular portion 6, through the vent hole 14 and into the air passageway 9 before passing into the user's mouth. At the same time, the movement of the actuator 19 causes the nozzle opening 13 to come into alignment with the mouthpiece 11. Further depression of the dispensing container 3 causes the lower end of the actuator 19 to come into contact with the end cap 25 at which point further downward axial movement of the actuator 19 is prevented. Thus, the end cap 25 forms an end stop for the actuator 19. Once the gap 27 has been traversed, further depression of the dispensing container 3 causes the valve stem 4 of the dispensing container 3 to be depressed and a dose of the medicament or other product to be discharged from the dispensing container 3 via the valve stem 4 into the socket 12, into the duct 18 and out through the nozzle opening 13 providing a fine aerosol mist which is inhaled by the user.

The inhalation apparatus is designed to be manually operated in a single fluid motion. The presence of the gap 27 provides "lost motion" which ensures that there is a time delay between the start of inhalation and the discharge of the medicament. Hence the presence of the gap 27 and the dimensioning of the actuator 20 and end cap 25 comprise a means for delaying discharge of the medicament upon depression of the container 3. The correct timing of the dispensing of the dosage of the medication is ensured by the correct dimensioning of the gap 27 between the actuator base 16 and the end cap 25. A larger gap 27 will produce a longer delay before discharge. Thus, the timing of the discharge of the medicament can be accurately controlled. The gap can be different for inhalers delivering different medication if this is required.

All of the components of the apparatus 1 may be plastics mouldings. Alternatively, the sealing disc 21 may be manufactured from a rubberised or similar material.

It will be appreciated that various modifications to the construction of the apparatus 1 may be made without departing from the scope of the invention.

What is claimed is:

1. An inhalation apparatus for dispensing a product comprising a housing having a portion adapted to receive a pressurised dispensing container and a mouthpiece, said apparatus further comprising a duct communicating with the container receiving portion for conveyance of product towards the mouthpiece, air inlet valve means comprising at least one air inlet for allowing air into the housing and a manually operated airflow controller for mechanically coordinating inhalation and dispensation of product, said airflow controller being biased to a first position sealing said air inlet and being manually movable to a second position in which the air inlet is unsealed and allows air to flow into the housing and through the mouthpiece when a user applies suction to the mouthpiece, said airflow controller being manually movable to a third position for the dispensing of a product into the resulting air flow, the movement between the second and third positions providing means for delaying the discharge of the product until the air flow has been established.

2. An inhalation apparatus as claimed in claim 1 wherein the airflow controller provides a bore for receiving, in use, a valve stem of a dispensing container, said duct connecting the bore with the mouthpiece.

3. An inhalation apparatus as claimed in claim 1 wherein the housing comprises a partition separating the housing into an upper cylindrical portion for receiving a dispensing container and a lower portion housing the airflow controller, wherein the air inlet is located in the partition and the airflow controller has a sealing disc engagable with said partition to cover the air inlet.

4. An inhalation apparatus as claimed in claim 3 wherein the airflow controller is axially slidable within a socket provided on the partition and is biased by a spring so that the sealing disc is in sealing contact with the partition.

5. An inhalation apparatus as claimed in claim 1 wherein movement of the air flow controller between the first and third positions comprises lost motion.

6. An inhalation apparatus as claimed in claim 1 wherein stop means are provided by an end cap of the housing to prevent movement of the air flow controller beyond the third position.

7. An inhalation apparatus as claimed in claim 4, including a dispensing container provided with a valve stem which is depressed in use, wherein the spring constant of the spring is such that a greater force is required to depress said valve stem than to compress the spring.

8. An inhalation apparatus as claimed in claim 2 wherein movement of the air flow controller between the first and third positions comprises lost motion.

9. An inhalation apparatus as claimed in claim 2 wherein stop means are provided by an end cap of the housing to prevent movement of the air flow controller beyond the third position.

10. An inhalation apparatus as claimed in claim 2 wherein the housing comprises a partition separating the housing into an upper cylindrical portion for receiving a dispensing container and a lower portion housing the airflow controller, wherein the air inlet is located in the partition and the airflow controller has a sealing disc engageable with said partition to cover the air inlet.

11. An inhalation apparatus as claimed in claim 10 wherein the airflow controller is axially slidable within a socket provided on the partition and is biased by a spring so that the sealing disc is in sealing contact with the partition.

12. An inhalation apparatus as claimed in claim 11, including a dispensing container provided with a valve stem which is depressed in use, wherein the spring has a spring constant which is such that a greater force is required to depress said valve stem than to compress the spring.

13. An inhalation apparatus according to claim 1 including a dispensing container provided with a valve stem which is depressed to dispense product from the container, said dispensing container being manually movable to move said airflow controller to said second and third positions, said container being operable to discharge product through the valve stem when said dispensing container is moved when said airflow controller is in said third position.

14. A method of operating an inhalation apparatus comprising the steps of inserting a pressurised dispensing container into a housing such that a valve stem of the dispensing container is received in a first end of an airflow controller, inserting a mouthpiece of the housing into the user's mouth and inhaling, wherein the flow of air into the mouthpiece is initially prevented by the airflow controller in a first position thereof sealing an air inlet means, depressing the dispensing container to cause the airflow controller to move to a second position away from the air inlet means to allow air to flow into the mouthpiece and further depressing the dispensing container to move the air flow controller to a third position causing the valve stem to depress and allowing medicament to be dispensed from the container into the mouthpiece to mix with the inhaled air.

* * * * *